US007138245B2

(12) United States Patent
Binder et al.

(10) Patent No.: US 7,138,245 B2
(45) Date of Patent: Nov. 21, 2006

(54) FXIII DETECTION FOR VERIFYING SERUM SAMPLE AND SAMPLE SIZE AND FOR DETECTING DILUTION

(75) Inventors: Steven R. Binder, Berkeley, CA (US); Jodi L. Goodrich, Martinez, CA (US); Zara Safarian, Pleasant Hill, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 12 days.

(21) Appl. No.: 10/965,608

(22) Filed: Oct. 13, 2004

(65) Prior Publication Data

US 2005/0106632 A1    May 19, 2005

Related U.S. Application Data

(62) Division of application No. 10/263,436, filed on Oct. 1, 2002, which is a division of application No. 09/872,639, filed on May 31, 2001, now Pat. No. 6,660,486.

(51) Int. Cl.
*G01N 33/53* (2006.01)
(52) U.S. Cl. .......................... 435/7.1; 435/4; 435/7.92
(58) Field of Classification Search ................ 435/7.1, 435/4–7.95, 973; 436/514–548, 8–16, 2; 422/50–73
See application file for complete search history.

(56) References Cited

U.S. PATENT DOCUMENTS

| | | | |
|---|---|---|---|
| 4,325,867 A | 4/1982 | Eberle et al. | |
| 4,601,977 A | 7/1986 | Ogawa et al. | |
| 4,624,927 A | 11/1986 | Fukushima et al. | |
| 5,015,588 A | 5/1991 | Lee et al. | |
| 5,401,638 A | 3/1995 | Carney et al. | |
| 5,688,919 A | 11/1997 | Hock | |
| 5,981,180 A | 11/1999 | Chandler | |
| 6,660,486 B1 | 12/2003 | Binder et al. | |

OTHER PUBLICATIONS

Katona et al., "Enzyme-linked immunosorbent assay for the determination of blood coagulation factor XIII A-subunit in plasma and in cells lysates", Journal of Immunological Methods 258 (2001), 127-135.*

(Continued)

*Primary Examiner*—James Housel
*Assistant Examiner*—Amy Lam
(74) *Attorney, Agent, or Firm*—M. Henry Heines; Townsend and Townsend and Crew, LLP

(57) ABSTRACT

Analyses of serum samples for the presence and amount of either of the two subunits of human Factor XIII protein are used as a means of eliminating a significant source of error that arises in the testing of serum and plasma. For serum samples, a negative result of an analysis for the presence of subunit a is a means of verifying that a sample is indeed serum, while a negative or positive result for subunit a serves to distinguish serum (negative) from plasma (positive). A positive result for the presence of subunit b is a means of verifying that the sample is either serum or plasma and not any other biological fluid. A quantitative analysis of subunit b is a means of verifying that the sample is of the intended volume rather than having been reduced in volume due to improper sampling. A quantitative analysis of subunit b is also a means of verifying the dilution of a sample of either serum or plasma.

5 Claims, 4 Drawing Sheets

OTHER PUBLICATIONS

. Murdock et al., "Development and Evaluation of ELISAS for Factor XIIIA and XIIIB Subunits in Plasma", Thrombosis Research, 67; 73-79, 1992.*

Ariens, et al., "Subunit Antigen and Activity Levels of Blood Coagulation Factor XIII in Healthy Individuals", Arterioscler. Thromb. Vasc. Biol., Aug. 1999, pp. 2012-2016.*

Katona et al., "Simple, Quick One-step ELISA Assay for the Determination of Complex Plasma Factor XIII (A2B2)", Thromb. Haemost. 2000, 83: 268-73.*

Kroll, The subunit composition of factor XIII proteins in normal and factor XIII deficient plasma and serum analysed by line immunmoelectrophoresis:Clinica Chemical Acta (1989); vol. 179 pp. 279-284.

Yorifuji et al., B Protein of factor XIII: differentiation between free B and complexed B; Blood (1998); vol. 72 pp. 1645-1650.

Achyuthan, K.E. et al. "A microtiter plate assay for factor XIII A-chain-fibrin interactions," Anal. Biochem. 1994, pp. 43-48, vol. 219.

Ariens et al.; "Subunit antigen and activity levels of blood coagulation factor XIII in healthy individuals: Relation to sex, age, smoking, and hypertension"; 1999, *Arteriosclerosis Thromobosis and Vascular Biology*, vol. 19, pp. 2012-2016.

Jenny and Jackson-Tarentino, "Causes of unsatisfactory performance in proficiency testing," *Clinical Chemistry* (2000) 46(1):89-99.

Gniewek et al., Monoclonal Antibodies specific for Human Plasma Factor XIII B-subunit and their use in Purification of Human Plasma Factor-XIII by Immunoaffinity Chromatography, *Federation Proceedings* (1985) 44 (4): 1070.

Katona et al.; "A simple quick one step ELISAS for Factor XIIIA and XIIIB subunits in plasma"; 1992, *Thrombosis Research*, vol. 67, pp. 268-273.

Kasahara, K. et al., ""A" subunit of factor XIII present on bovine platelet membrane and mediates collagen-induced platelet activation," *Thrombosis Res.* 1988, pp. 253-263, vol. 50.

Mitkevich, O.V. et al., "Coagulation factor XIIIa undergoes a conformational change evoked by glutamine substrate," *J. Biol. Chem.* Jun. 5, 1998, pp. 14387-14391, vol. 273, No. 23.

Murdock et al., "Development and evaluation of elisas for factor XIIIA and XIIIB subunits in plasma," *Thrombosis Research* (1992) 67:73-79.

Musbek et al.; "Novel aspects of blood coagulation factor XIII. I. Structure, distribution, activation, and function"; 1996, *Critical Reviews in Clinical Laboratory Sciences*, vol. 33, pp. 357-421.

Nagy et al.; "Biosynthesis of factor XIII B subunit"; 1986, *Blood*, vol. 68, pp. 1272-1279.

Nonaka et al.; "Molecular cloning of the b subunit of mouse coagulation factor XIII and assignment of the gene to chromosome 1: Close evolutionary relationship to complement factor H"; 1993, *Genomics*, vol. 15, pp. 535-542.

Schweinie, J.E. et al.; Monoclonal Antibodies Specific for Human Plasma Factor XIII B Subunit and Their Use in the Purification of Human Plasma Factor XIII by Immunoaffinity Chromatography; *Blood Coagulation*, abstract No. 3857.

Takagi, J. et al. "Subunit B of factor XIII is present in bovine platelets," *Thrombosis Res.* 1988, pp. 767-774, vol. 50.

* cited by examiner

FXIII DETECTION FOR VERIFYING SERUM SAMPLE AND SAMPLE SIZE AND FOR DETECTING DILUTION

CROSS REFERENCE TO RELATED APPLICATIONS

This application is a division of co-pending application Ser. No. 10/263,436, filed Oct. 1, 2002, which is a division of then application Ser. No. 09/872,639, filed May 31, 2001, now U.S. Pat. No. 6,660,486. The contents of both patent application Ser. No. 10/263,436 and patent application Ser No. 09/872,639 are incorporated herein by reference.

BACKGROUND OF THE INVENTION

1. Field of the Invention

This invention resides in the fields of quality control for clinical laboratory test procedures and instrumentation, and of human Factor XIII protein and its uses.

2. Description of the Prior Art

The medical community, including practicing physicians, researchers, and clinicians of all types rely on the clinical laboratory for analytical testing of biological samples as part of routine physical examinations, and in diagnosing disease and monitoring patient progress and disease conditions, as well as similar functions and services. Among the most common biological samples that are analyzed by these laboratories are serum and plasma, although other fluids such as urine and cerebrospinal fluid are often used as well. Many analyses are performed by automated instrumentation, and in some cases large numbers of samples are analyzed simultaneously. Whether the tests are performed in this manner or on an individual basis by a laboratory technician, there are numerous sources of error that can produce spurious results.

The error that arises falls within two general classes—(1) spurious test results due to lapses in standard operating procedures and instrument malfunctions, and (2) analytic error. Some of the most common errors of the first class are those due to inaccurate mathematical correction for specimen dilution, misinterpretation of instrument codes, and instrument sampling errors such as bubbles in sample wells or transfer tubing or other malfunctions that result in samples whose volumes are less than standard. Of the second class, the most common type of error is that caused by calibration drift. This invention addresses errors of the first class. In proficiency testing, these errors have been shown to account for 300 false test results per one million assays. A review of the causes of laboratory errors is reported by Jenny, R. W., et al., "Causes of Unsatisfactory Performance in Proficiency Testing," *Clin. Chem.* 46(1): 89–99 (2000), who found that inaccurate dilution corrections accounted for 21% of spurious test results in proficiency testing, and missampling in a particular automated instrument such as might be caused by air bubbles or sample clotting occurred 0.016% of the time, during use of the instrument in testing for samples from the general population. A further source of error is the use of an incorrect sample type, such as urine, cerebrospinal fluid, or other bodily fluids instead of serum, or in coagulation studies the failure to differentiate between serum and plasma.

SUMMARY OF THE INVENTION

It has now been discovered that analysis of a biological sample for human Factor XIII protein is an effective way of detecting various errors of the types discussed above. The two subunits of the protein, hereinafter referred to as "subunit a" or "FXIIIa," which is recognized in the art as the activated form of the protein, and "subunit b" or "FXIIIb," whose function is generally unknown although speculated to be that of a carrier protein, are analyzed separately in different aspects of this invention, providing different types of information useful in detecting error. The whole FXIII is a tetramer containing two of each of the subunits, and the tetramer as well as the dissociated forms of each subunit are present in human plasma. Immunoassays of human serum, however, detect neither the tetramer nor dissociated subunit a, but instead detect only subunit b. A small amount of tetramer may be present in human serum, but if so, the amount is below the detection limit of a typical immunoassay. The terms "serum" and "plasma" as used herein refer to human serum and plasma unless otherwise noted.

In one aspect, the present invention resides in a utilization of the fact that subunit b has a narrow physiological range in both plasma and serum and is only rarely deficient. In addition, disease states have sufficiently little effect on the concentration of this subunit. Accordingly, this aspect of the invention resides in a quantitative determination of the subunit b in a sample of serum or plasma as an indication of the amount or volume of that sample. If the amount of subunit b detected is significantly less than would be present in the sample if the sample were of the intended volume, the determination serves as an indication of a sampling volume error, i.e., a shortage relative to the intended volume of the sample.

In another aspect, this invention resides in a method for determining whether a sample is serum or plasma, or for verifying that the sample is indeed serum rather than plasma, by analyzing the sample for subunit a, whose presence serves as an indication that plasma constitutes at least part, if not all, of the sample composition.

In a third aspect, the invention resides in a method for verifying that a sample that is thought to be serum or plasma is indeed one of these two rather than another biological fluid such as cerebrospinal fluid or urine or non-human serum. This determination is achieved by analyzing the sample for the presence of subunit b, a positive result indicating that the sample is indeed serum or plasma, since subunit b is present in both serum and plasma and is not present in non-human serum or in other biological fluids.

A still further aspect of the invention resides in the analysis of a sample of serum or plasma for the quantity or concentration of subunit b in that sample to determine or verify the degree of dilution of the sample. This is achieved by comparing the quantity or concentration detected with that of a sample of the same type of fluid but whose degree of dilution is known.

These and other features and aspects of the invention will be more readily understood from the following description.

DETAILED DESCRIPTION OF THE INVENTION AND SPECIFIC EMBODIMENTS

Figure 1:
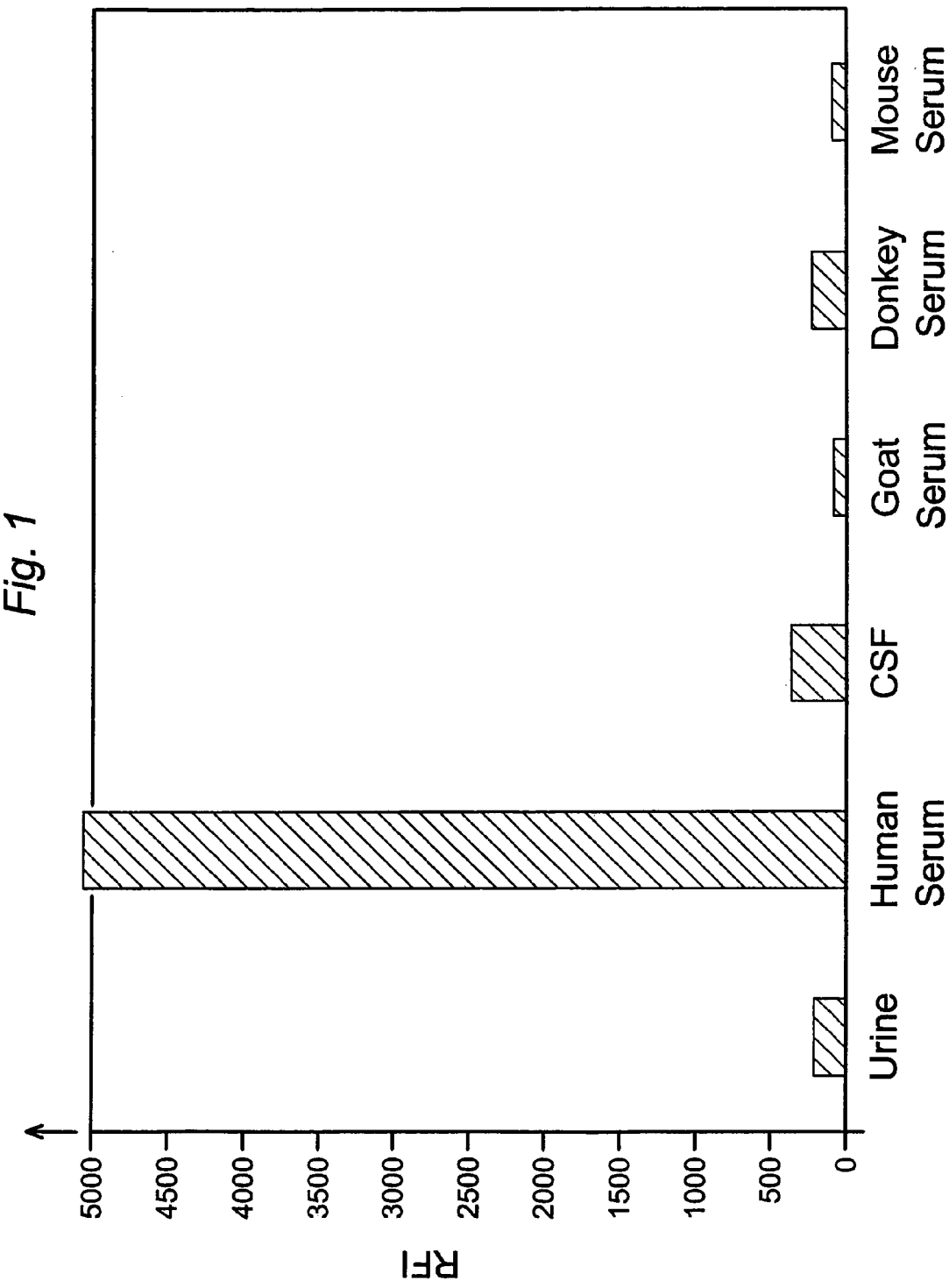
FIG. 1 is a bar graph comparing FXIII levels in human serum, urine, cerebrospinal fluid, and non-human sera.

Human blood coagulation factor XIII (FXIII) is a transglutaminase and the last enzyme in the blood coagulation cascade. Also known as fibrin-stabilizing factor, Laki-Lorand factor, fibrinase, and crosslinking enzyme, FXIII is responsible for crosslinking the blood clot by catalyzing the formation of isopeptide bonds between the side chains of glutamine and lysine. This crosslinking occurs mainly between fibrin molecules in the soft clot but also between fibrin and antiplasmin. The factor itself is normally present as the tetramer described above, which is a zymogen that performs its enzymatic function only upon activation by thrombin and $Ca^{++}$. Activation occurs through thrombin cleavage of the Arg 37-Gly 38 peptide bond near the amino terminus of the a subunits. In the presence of $Ca^{++}$ ions, the b subunits then dissociate from the tetramer, unmasking the a subunit. The activated form is thus the liberated a subunit, FXIIIa. The b subunit, FXIIIb, is thought to protect or stabilize the a subunit in the tetramer or to regulate the activation of the tetramer in blood plasma. Once activated, the a subunit remains attached to fibrin, and the b subunit is released into the serum. Neither the tetramer nor any of the individual subunits are present in urine or cerebrospinal fluid, or non-human bodily fluids, that may be used as analytical samples for purposes of diagnosis or monitoring.

Within the detection limits of conventional immunoassay techniques, therefore, free FXIIIb exists in both serum and plasma (and no other bodily fluids), while free FXIIIa and the tetramer (containing two chains each of FXIIIa and FXIIIb) exist only in plasma, i.e.:

Plasma: FXIIIa, FXIIIb, and tetramer

Serum: FXIIIb only

The typical concentration of FXIIIb in serum is 21 µg/mL, and any variations in patients who are not suffering from congenital FXIII deficiency are within the range of approximately 10–40 µg/mL. The concentration is independent of the pathophysiological conditions of the body and unaffected by the coagulation process.

While various methods can be used to detect and/or quantitate either the tetramer or the two subunits, a preferred method of detection is immunoassay. A particularly convenient class of immunoassays are those in which the test sample is contacted with a binding reagent that is immobilized on a solid phase, and one of the steps performed to detect the presence and/or amount of the analyte is the separation of the species in the reaction mixture that have become bound to the solid-phase binding reagent from species that remain unbound. The solid phase may assume any of a variety of forms, the most prominent examples of which are the walls of a reaction vessel, such as the individual wells of a multi-well plate, and solid particles that are dispersed in the assay mixture.

When particles are used, they are preferably microscopic in size, and therefore referred to as microparticles. The microparticles are generally formed of a polymeric material that bears certain characteristics that make it useful in immunoassays. One such characteristic is that the matrix be inert to the components of the biological sample and to the assay reagents other than the assay reagent that is affixed to the microparticle. Other characteristics are that the matrix be solid and insoluble in the sample and in any other solvents or carriers used in the assay, and that it be capable of affixing an assay reagent to the microparticle. When the immunoassay is designed such that fluorescence will be used as the means of detection, the polymeric material is preferably one that exhibits minimal autofluorescence. Examples of suitable polymers are polystyrenes, polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle. These considerations are also applicable to solid phases other than microparticles.

The use of particles further offers the ability to classify particles into groups that are distinguishable by instrumentation. Multiple assays can therefore be performed simultaneously, with separate assay results independently determined for each group of particles. Classification of particles in this manner can be achieved by embedding identifying agents such as fluorochromes or dyes in the body of each particle, using different such agents, different intensities of such agents, or combinations of such agents at different ratios among the different groups of particles. Flow cytometers that can distinguish among particles on these bases are known in the art and available from commercial suppliers.

The surface of the solid phase will preferably contain functional groups for attachment of the binding member, typically an antibody, that binds the analyte. These functional groups can be incorporated into the polymer structure by conventional means, such as the forming the polymer from monomers that contain the functional groups, either as the sole monomer or as a co-monomer. Examples of suitable functional groups are amine groups ($-NH_2$), ammonium groups ($-NH_3^+$ or $-NR_3^+$ where R is an alkyl or aryl group), hydroxyl groups ($-OH$), carboxylic acid groups ($-COOH$), and isocyanate groups ($-NCO$). Useful monomers for introducing carboxylic acid groups into polystyrenes, for example, are acrylic acid and methacrylic acid.

Attachment of the binding member to the solid phase surface can be achieved by electrostatic attraction, specific affinity interaction, hydrophobic interaction, or covalent binding. Covalent binding is preferred. Linking groups can be used as a means of increasing the density of reactive groups on the solid phase surface and decreasing steric hindrance to achieve maximal range and sensitivity for the assay, or as a means of adding specific types of reactive groups to the solid phase surface to broaden the range of types of assay reagents that can be affixed to the solid phase. Examples of suitable useful linking groups are polylysine, polyaspartic acid, polyglutamic acid and polyarginine.

In embodiments in which particles are used as the solid phase and detection is performed by flow cytometry, care should be taken to avoid the use of particles that emit high autofluorescence since this renders them unsuitable for flow cytometry. Particles of low autofluorescence can be created by standard emulsion polymerization techniques from a wide variety of starting monomers. Particles of high porosity and surface area (i.e., "macroporous" particles), as well as particles with a high percentage of divinylbenzene monomer, should be avoided since they tend to exhibit high autofluorescence. Generally, however, microparticles suitable for use in this invention can vary widely in size, and the sizes are not critical to this invention. In most cases, best results will be obtained with microparticle populations whose particles range from about 0.3 micrometers to about 100 micrometers, preferably from about 0.5 micrometers to about 20 micrometers, in diameter.

When particles are used as the solid phase, one means of separating bound from unbound species is to use particles that are made of or that include a magnetically responsive material. Such a material is one that responds to a magnetic field. Magnetically responsive materials that can be used in the practice of this invention include paramagnetic materials, ferromagnetic materials, ferrimagnetic materials, and metamagnetic materials. Paramagnetic materials are preferred. Examples are iron, nickel, and cobalt, as well as metal oxides such as $Fe_3O_4$, $BaFe_{12}O_{19}$, CoO, NiO, $Mn_2O_3$, $Cr_2O_3$, and CoMnP. The magnetically responsive material may constitute the entire particle, but is preferably only one component of the particle, the remainder being a polymeric material to which the magnetically responsive material is affixed and which is chemically derivatized as described above to permit attachment of an analyte binding member.

When particles containing magnetically responsive material are used, the quantity of such material in the particle is not critical and can vary over a wide range. The quantity can affect the density of the particle, however, and both the quantity and the particle size can affect the ease of maintaining the particle in suspension. Maintaining suspension serves to promote maximal contact between the liquid and solid phase and to facilitate flow cytometry. In assays where fluorescence plays a role in the detection, an excessive quantity of magnetically responsive material in the particles will also produce autofluorescence at a level high enough to interfere with the assay results. It is therefore preferred that the concentration of magnetically responsive material be low enough to minimize any autofluorescence emanating from the material. With these considerations in mind, the magnetically responsive material in a particle in accordance with this invention preferably ranges from about 1% to about 75% by weight of the particle as a whole. A more preferred weight percent range is from about 2% to about 50%, a still more preferred weight percent range is from about 3% to about 25%, and an even more preferred weight percent range is from about 5% to about 15%. The magnetically responsive material can be dispersed throughout the polymer, applied as a coating on the polymer surface or as one of two or more coatings on the surface, or incorporated or affixed in any other manner that secures the material in the polymer matrix.

Immunoassays of both the competitive type and the sandwich type can be used. Competitive assays for example can be performed by using solid phase to which molecules of a binding protein (such as an antibody) specific for the analyte are bound. During the assay, the sample and a quantity of labeled analyte, either simultaneously or sequentially, are contacted with the solid phase. By using a limited number of binding sites on the solid phase, the assay causes competition between the labeled analyte and the analyte in the sample for the available binding sites. After a suitable incubation period, the mixture of liquid and solid are separated. If particles containing a magnetically responsive material are used as the solid phase, separation is achieved by placing the particles in a magnetic field, causing the particles to adhere to the walls of the reaction vessel. Otherwise, separation can be achieved by centrifugation or other conventional methods well known among those skilled in the use and design of immunoassays. The particles once separated are washed to remove any remaining unbound analyte and label. The particles can then be resuspended in a carrier liquid for introduction into a flow cytometer where the label is detected.

Sandwich assays, also known as immunometric assays, are performed by using particles (or any solid phase) to which antibody to the analyte is bound. This antibody is termed "capture" antibody. An excess of capture antibody is used relative to the suspected quantity range of the analyte so that all of the analyte binds. The solid phase with capture antibody attached is placed in contact with the sample, and a second antibody to same analyte is added, simultaneously or sequentially with the sample. Like the capture antibody, the second antibody is in excess relative to the analyte, but unlike the capture antibody, the second antibody is conjugated to a detectable label, and may hence be referred to as "label" antibody. The capture and label antibodies bind to different epitopes on the analyte or are otherwise capable of binding to the analyte simultaneously in a non-interfering manner. After a suitable incubation period, solid and liquid phases are separated. In the case where the solid phase consists of magnetically responsive microparticles, the liquid mixture with microparticles suspended therein is placed under the influence of a magnetic field, causing the microparticles to adhere to the walls of the reaction vessel, and the liquid phase is removed. The microparticles, still adhering to the vessel wall, are then washed to remove excess label antibody that has not become bound to the immobilized analyte, and the microparticles are then resuspended in a carrier liquid for introduction into a flow cytometer where the amount of label attached to the particles through the intervening analyte is detected.

Immunoassays in the practice of this invention can involve the use of either monoclonal antibodies or polyclonal antibodies. Antibodies with specific binding affinity for either of the two subunits (individually) of FXIII and antibodies for the tetramer are available from commercial suppliers. Such suppliers include Biogenesis Inc., Brentwood, N.H., USA; Affinity Biologics, distributed by U.S. Enzyme Research Laboratories; Calbiochem, San Diego, Calif., USA; The Binding Site, Inc., San Diego, Calif., USA; Biodesign International, Saco, Me., USA; Enzyme Research Laboratories, Inc., South Bend, Ind., USA; Fitzgerald Industries International Inc., Concord, Mass., USA; and Hematologics Inc., Seattle, Wash., USA. In sandwich assays, antibodies can be used in various combinations as capture and label antibodies. Thus, to quantify FXIIIa, anti-FXIIIa can be used as the capture antibody and anti-FXIII (i.e., antibody to the tetramer) as the label antibody. Likewise, anti-FXIII (i.e., antibody to the tetramer) can be used as the capture antibody and anti-FXIIIa as the label antibody. Alternatively, anti-FXIIIa can be used as both capture antibody and label antibody provided that the capture and label antibodies have specificities to different epitopes on the FXIIIa molecule. To quantify FXIIIb, anti-FXIIIb can be used as the capture antibody and anti-FXIII (i.e., antibody to the tetramer) as the label antibody. Likewise, anti-FXIII (i.e., antibody to the tetramer) can be used as the capture antibody and anti-FXIIIb as the label antibody. And likewise further, anti-FXIIIb can be used as both capture antibody and label antibody provided that the capture and label antibodies have specificities to different epitopes on the FXIIIb molecule. Other combinations will be readily apparent to those skilled in the art. Either polyclonal or monoclonal antibodies may be used. When monoclonal antibodies are used, they may be either the capture antibody, the label antibody, or both.

Detection of the analyte in the practice of this invention can be accomplished by any of the wide variety of detection methods that are used or known to be effective in immunological assays. Fluorescence is one example and is readily achieved by the use of fluorophore labels. The wide variety of fluorophores and methods of using them in immunoassays are well known to those skilled in the immunoassay art, and a wide variety of fluorophores are commercially available. The preferred fluorophores are those that contribute as little autofluorescence as possible. The fluorophore phycoerythrin is preferred in this regard, since its extinction coefficient and quantum yield are superior to those of other fluorophores.

For embodiments of the invention that entail the use of flow cytometry, methods of and instrumentation for flow cytometry are known in the art. Examples of descriptions of flow cytometry instrumentation and methods in the literature are McHugh, "Flow Microsphere Immunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Md., USA: Williams and Williams, 1993), pp. 535–544; Lindmo et al., "Immunometric Assay Using Mixtures of Two Particle Types of Different Affinity," *J. Immunol. Meth.* 126: 183–189 (1990); McHugh, "Flow Cytometry and the Application of Microsphere-Based Fluorescence Immunoassays," *Immunochemica* 5: 116 (1991); Horan et al., "Fluid Phase Particle Fluorescence Analysis: Rheumatoid Factor Specificity Evaluated by Laser Flow Cytophotometry," *Immunoassays in the Clinical Laboratory*, 185–189 (Liss 1979); Wilson et al., "A New Microsphere-Based Immunofluorescence Assay Using Flow Cytometry," *J. Immunol. Meth.* 107: 225–230 (1988); Fulwyler et al., "Flow Microsphere Immunoassay for the Quantitative and Simultaneous Detection of Multiple Soluble Analytes," *Meth. Cell Biol.* 33: 613–629 (1990); Coulter Electronics Inc., United Kingdom Patent No. 1,561,042 (published Feb. 13, 1980); Steinkamp et al., *Review of Scientific Instruments* 44(9): 1301–1310 (1973); and Chandler, V. S., et al., U.S. Pat. Ser. No. 5,981,180 "Multiplexed Analysis of Clinical Specimens Apparatus and Methods," issued Nov. 9, 1999 (Luminex Corporation).

This invention is useful in both manual procedures and automated procedures. The invention is of particular interest in verifying the accuracy of automated immunoassay analyzers. Examples of such instruments are the AxSYM immunoassay analyzer of Abbott Laboratories Diagnostics Division, Abbott Park, Ill., USA, and the CODA® immunoassay analyzer of Bio-Rad Laboratories, Inc., Hercules, Calif., USA.

The methods of this invention can be used in conjunction with any analytical procedures that are to be performed on serum or plasma samples, for analytes indicative of a wide variety of physiological and clinical conditions. The FXIII subunit analysis will verify the accuracy of the sampling volume or the dilution or that the correct sample is being analyzed. The two analyses can be performed either simultaneously or sequentially.

The following examples are offered for illustrative purposes only, and are not intended to limit the scope of the invention.

EXAMPLE 1

This example provides the results of sequential immunoassays performed on microparticles to illustrate the ability of the present invention to distinguish plasma from serum by analyzing for the presence of dissociated subunit a of human Factor XIII protein.

The assays were sandwich-type immunoassays and the microparticles were 7.1 µm magnetic microparticles. A portion of the microparticles was coated with polyclonal anti-FXIIIa$_2$b$_2$ antibody and a second portion was coated with polyclonal anti-FXIIIa antibody (as capture antibodies). The polyclonal anti-FXIIIa$_2$b$_2$ antibody was specifically reactive toward the tetramer, while the polyclonal anti-FXIIIa antibody was reactive toward both free and bound a subunit and non-reactive toward free b subunit. A different polyclonal anti-FXIIIa$_2$b$_2$ antibody was used as the label antibody for the tests on both portions. Assays on the first portion of microparticles thus indicated the presence of the tetramer and any dissociated subunits, while assays on the second portion indicated the presence of dissociated subunit a only.

The microparticles were styrene crosslinked with divinylbenzene and containing magnetite. The particle surfaces were carboxylated with a coating layer. Varying amounts of fluorochromes were embedded in each particle set to give each group of particles a unique spectral address or to color-code the particles. The particle coatings were converted into active ester form by reaction with 1-ethyl-3-(3-dimethylaminopropyl)carbodiimide hydrochloride and N-hydroxysulfosuccinimide. The active ester-coated particles were then coupled to antibody at a free amino group on the antibody. The conversion to active ester form and the coupling of antibody were performed according to conventional procedures well known among immunologists.

Label antibody was prepared by conjugating antibody to phycoerythrin after first activating the antibody with succinimidyl 4-(N-maleimidomethyl)cyclohexane 1-carboxylate and activating the phycoerythrin with sulfosuccinimidyl 6-[3'-(2-pyridyldithio)-propionamido]hexanoate/dithiothreitol. These activations and conjugation were likewise performed according to conventional procedures well known among immunologists.

For the first assay (using polyclonal anti-FXIIIa$_2$b$_2$ antibody as both the capture and label antibody), 100 µL of serum was mixed with 100 µL of a particle suspension in wash buffer in which the particle concentration was 47 µg/mL, while 100 µL of plasma was mixed with 100 µL of a 47 µg/mL particle suspension to form a separate suspension. For the second assay (using polyclonal anti-FXMa antibody as the capture antibody and polyclonal anti-FXIIIa$_2$b$_2$ antibody as the label antibody), serum and plasma were again mixed separately with the particles in the same proportions to form separate suspensions. In all cases, the particle/sample suspensions were incubated on a shaker (1,100 rpm) at room temperature for fifteen minutes. Unbound and contaminating proteins and immunoglobulins were removed by magnetic separation and washed twice with wash buffer, with three-minute magnetic separations followed by aspirations between the washes. A final 75-µL volume of wash buffer was added to each group for the analyses.

Analyses was performed on a Luminex 100 flow cytometer capable of measuring forward light scatter and particle fluorescence. The excitation system of the instrument included a 532 nm reporter laser for excitation of the phycoerythrin at the microparticle surface, and a 635 nm classification laser for excitation of the fluorochomes embedded in the bulk of the microparticle. The fluorescent emissions that resulted from the excitations were discriminated with selective emission filters and converted into an output signal by a digital signal processor within the instrument, the value of the signal indicating the magnitude of the reaction in any particular immunoassay. The instrument was calibrated by calibration microparticles using appropriate procedures recommended by the instrument supplier. The values thus calibrated, which are indications of the relative magnitude of the fluorescence intensities are referred to herein as "detector units."

The results expressed in detector units for a series of individual samples of serum and plasma, as well as the wash buffer alone, are listed in Table I.

TABLE I

Immunoassays on Microparticles: Serum vs. Plasma

| | Detector Units | | | |
|---|---|---|---|---|
| | Polyclonal Anti-FXIIIa$_2$b$_2$ Antibody as Both Capture and Label | | Polyclonal Anti-FXIIIa Antibody as Capture and Polyclonal Anti-FXIIIa$_2$b$_2$ Antibody as Label | |
| Sample | Serum | Plasma | Serum | Plasma |
| A | 1906.5 | 320.8 | 341.0 | 4053.5 |
| B | 1839.5 | 720.3 | 419.0 | 3997.8 |
| C | 1549.3 | 791.5 | 363.5 | 4958.0 |
| D | 1817.0 | 750.0 | 287.3 | 4610.5 |
| E | 2136.3 | 985.0 | 623.5 | 4482.0 |
| F | 1797.0 | 758.3 | 504.0 | 4415.5 |
| G | 2233.5 | 1100.5 | 679.3 | 5062.8 |
| H | 2138.5 | 972.3 | 462.0 | 5020.5 |
| I | 3175.3 | 2195.5 | 503.3 | 6044.0 |
| J | 2073.8 | 921.3 | 468.8 | 5158.0 |
| K | 1933.8 | 777.0 | 392.8 | 4692.5 |
| L | 1921.0 | 890.0 | 509.0 | 4782.5 |
| Wash Buffer | 243.3 | | 249.0 | |

The data in Table I demonstrate that equivalent FXIII signals were obtained in plasma and serum when both the capture and reporter antibodies had binding affinity to the tetramer (as well as the dissociated subunits), and that no signal was detected in serum when the capture antibody was specific to the a subunit. The uniqueness of the a subunit to plasma (i.e., the absence of the a subunit in serum) thus distinguished plasma from serum.

EXAMPLE 2

This example provides the results of ELISAs (enzyme-linked immunosorbent assays) to illustrate the ability of the present invention to distinguish plasma from serum, this time using monoclonal antibody specific for the tetramer as the capture antibody in all cases, and polyclonal antibody specific for subunit a and polyclonal antibody specific for subunit b in separate assays as the detection antibody.

The assays were performed on coated microplates, and as in Example 1, two assays were performed on serum and two on plasma. To coat the plates, the capture antibody was diluted 1/100 with 50 mM carbonate buffer, pH 9.6, and added to the microplate wells in volumes of 100 µL per well, followed by incubation overnight at 4° C. per well. The wells were emptied immediately before use and blocking buffer was added, followed by four washes with phosphate-buffered saline (PBS) and Tween surfactant. Plasma and serum samples were diluted 1/400 with PBS and added to the wells. Detection antibody, diluted 1/1000 was then added to each well at 100 µL/well, and the microplates were incubated for sixty minutes at room temperature, washed with PBS-Tween, incubated again for sixty minutes at room temperature, then rewashed. Peroxidase-conjugated anti-rabbit IgG, diluted 1/1000, was added at 100 µL/well. The peroxidase substrate tetramethylbenzidine in an acidic buffer (100 µL) was then added to each well, and when the color developed, 100 µL of a stop solution was added to each well.

The optical density of each well was measured at 450 nm using an ELISA reader. The results are listed in Table II.

TABLE II

Immunoassays on Microplates: Serum vs. Plasma

| | Optical Density at 450 nm | | | |
|---|---|---|---|---|
| | Monoclonal Anti-FXIIIa$_2$b$_2$ Antibody as Capture and Polyclonal Anti-FXIIIa Antibody as Detecting Antibody | | Monoclonal Anti-FXIIIa$_2$b$_2$ Antibody as Capture and Polyclonal Anti-FXIIIb Antibody as Detecting Antibody | |
| Sample | Plasma | Serum | Plasma | Serum |
| A | 1.195 | 0.677 | 2.484 | 2.486 |
| B | 1.491 | 0.580 | 2.873 | 2.837 |
| C | 1.364 | 0.379 | 3.062 | 2.804 |

These data demonstrate that the a subunit was detected with antibody specific to that subunit only in plasma and not in serum, confirming once again that the uniqueness of the a subunit to plasma is a means of distinguishing plasma from serum.

EXAMPLE 3

This example compares the results of assays for the FXIII tetramer in human urine, human cerebrospinal fluid, and serum from various species.

The assays were sandwich-type immunoassays performed on magnetic microparticles as in Example 1, using monoclonal anti-human FXIIIa$_2$b$_2$ antibody as the capture antibody and polyclonal anti-human FXIIIa$_2$b$_2$ antibody conjugated with phycoerythrin as the label antibody. The particles, which were 8.0 µm in diameter, were coated with capture antibody in the manner described in Example 1, and antibody-label conjugates were likewise prepared as described in Example 1. The particles were suspended in wash buffer to a concentration of 47 µg/mL, and 100 µL aliquots of the particle suspensions were mixed with 100 µL each of human serum, cerebrospinal fluid, urine, donkey serum, mouse serum, and goat serum. The resulting particle/sample suspensions were incubated on a shaker (1,100 rpm) at room temperature for fifteen minutes. Unbound and contaminating proteins were then removed by magnetic separation. The particles were then washed twice, with three-minute magnetic separations and aspirations between washes. The prediluted conjugate (1.8 µg/test) was then added and the suspensions were incubated again (room temperature, fifteen minutes, 1,100 rpm), followed by magnetic separations and aspirations. Finally, wash buffer (75 µL) was added to prepare the particles for flow cytometry analysis.

Flow cytometry was then performed as in Example 1. The results are shown in bar-graph form in FIG. 1, where the bars, from left to right, represent human urine, human serum, human cerebrospinal fluid, goat serum, donkey serum, and mouse serum. The graph clearly shows that FXIII was detected only in human serum, and not in other human bodily fluids or in the sera of goat, donkey, or mouse.

EXAMPLE 4

This example illustrates how analyses for FXIII in accordance with this invention are used to detect short samples, i.e., differences in volumes of human serum samples. The same type of microparticles described above in Example 3 were used.

In a first set of tests, sample volumes of 50 μL, 10 μL, 3.2 μL, 2.0 μL, and 1 μL were added to microparticle suspensions (100 μL, 47 μg/mL in wash buffer). Incubations, washings and other procedural steps were performed as in Example 3, and the results, which were read on the Luminex flow cytometer as detector units, are shown in Table III.

TABLE III

Sample Volume Variation Tests: First Set

| Sample Volume (μL) | Detector Units |
|---|---|
| 50.0 | 3165.0 |
| 10.0 | 2459.8 |
| 3.2 | 2049.6 |
| 2.0 | 1967.3 |
| 1.0 | 1624.0 |

These results demonstrate that human serum samples that are deficient in size can be detected by analysis of the amount of FXIII.

In a second set of tests, sample volumes of the same size were adjusted to 100 μL with wash buffer before being added to the microparticle suspension. The procedure was otherwise the same as that used in the first set. The results are listed in Table IV.

TABLE IV

Sample Volume Variation Tests: Second Set

| Sample Volume (μL) Prior to Adjustment to 100 μL | Detector Units |
|---|---|
| 50.0 | 3087.8 |
| 10.0 | 2217.2 |
| 3.2 | 1618.8 |
| 2.0 | 1447.3 |
| 1.0 | 844.5 |

These results confirm those of the first set.

In a third set, sample volumes of 17 μL, 13 μL, 11 μL, 9 μL, 7 μL, 5 μL, and 3 μL were combined with 390 μL wash buffer, and 100 μL of each was added to the microparticle suspension. The procedure was otherwise the same as that used in the first and second sets, and the results are listed in Table V.

TABLE V

Sample Volume Variation Tests: Third Set

| Sample Volume (μL) Prior to Adding to 390 μL | Detector Units Sample No. | | | | | |
|---|---|---|---|---|---|---|
| | 1 | 2 | 3 | 4 | 5 | 6 |
| 17 | 1977.5 | 1757.0 | 2102.8 | 1647.5 | 2121.8 | 1724.8 |
| 13 | 1825.3 | 1624.0 | 1952.8 | 1541.5 | 1990.3 | 1696.5 |
| 11 | 1704.5 | 1482.3 | 1819.5 | 1459.5 | 1876.0 | 1526.5 |
| 9 | 1573.0 | 1332.5 | 1645.3 | 1313.0 | 1783.5 | 1393.3 |
| 7 | 1414.3 | 1246.0 | 1575.0 | 1179.0 | 1601.8 | 1423.5 |
| 5 | 1211.0 | 1022.5 | 1286.3 | 985.0 | 1396.8 | 1202.3 |
| 3 | 921.5 | 778.5 | 989.3 | 795.8 | 1075.0 | 1076.5 |
| 1 | 465.5 | 438.0 | 523.0 | 467.0 | 649.5 | 600.5 |

These results confirm the results of the first and second sets.

In a fourth set of tests, 23 serum samples (stored at −70° C.) with volumes of 5 μL, 3 μL, 2 μL, and 1 μL were combined with 295 μL wash buffer, and 100 μL of the coated particle suspension (0.28 μg) were added to each tube. The resulting particle/sample suspensions were incubated on a shaker at 900 rpm at room temperature for fifteen minutes. Unbound and contaminating proteins and immunoglobulins were removed by magnetic separation. The particles were washed twice with 300 μL wash buffer, with a three-minute magnetic separation and aspiration in between successive washes. After the final wash, 50 μL of phycoerythrin-labeled anti-FXIII (0.25 μg phycoerythrin per test) was added to each tube. The Tubes were incubated on a skaker at room temperature (15 minutes, 900 rpm), followed by a three-minute magnetic separation and aspiration. The particles were then washed twice with 300 μL wash buffer, with three-minute magnetic separations and aspirations between washes. Wash buffer (75 μL) was then added, and the suspension was analyzed on a flow cytometer.

Figure 3:
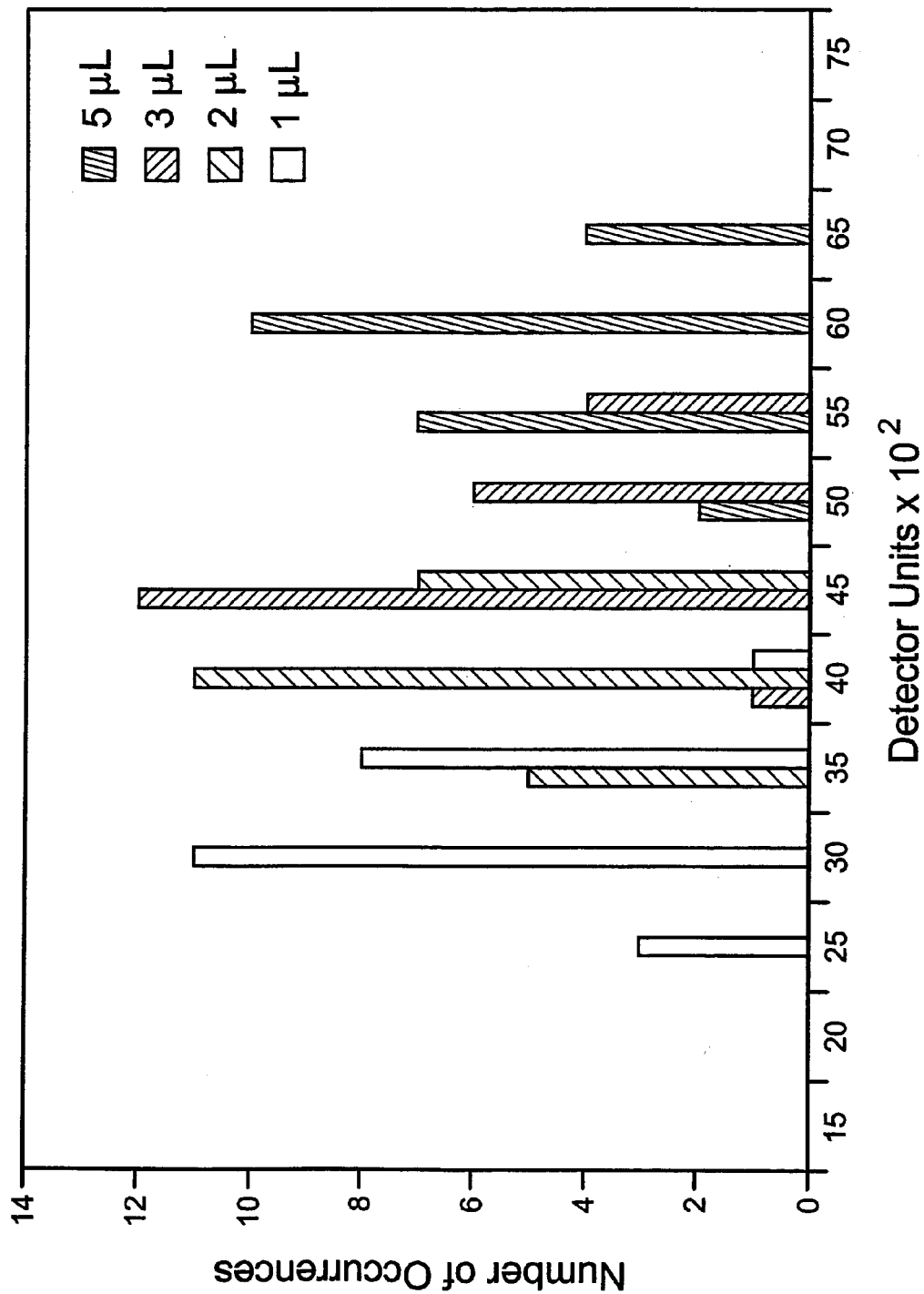
FIG. 3 is a histogram comparing FXIII levels among serum samples of different sample sizes.

The results are shown in FIG. 3 which shows the cytometer detector units and how they are distributed among the various sample sizes. The horizontal axis is the detector units and the vertical axis is the number of samples, and different sets of vertical bars are used for the various sample sizes, filled bars for 5 μL samples, open bars for 1 μL samples, shaded bars with lines slanting upward to the right for 3 μL samples, and shaded bars with lines slanting upward to the left for 2 μL samples. All 1 μL samples are fully distanced from all 5 μL samples, with no overlap between these two sets. This indicates that the presence of samples that are only 20% of the proper sample volume can be consistently distinguished from those that are full volume.

EXAMPLE 5

This example illustrates how analyses for FXIII in accordance with this invention are used to identify human serum samples that have been diluted. The same type of microparticles described above in Example 4 were used.

In a first set of tests, serum was used in dilutions of 1/10, 1/20, 1/40, 1/80, and 1/160 with wash buffer. Each dilution was mixed with a coated microparticle suspension as in the preceding examples. Magnetic separation was then performed immediately (without incubation) to remove contaminating proteins and immunoglobulins. After subsequent washes and incubation with labeled antibody, the microparticles were analyzed on the Luminex flow cytometer, and the results are shown in Table VI.

TABLE VI

Sample Dilution Tests: First Set

| Dilution | Detector Units |
|---|---|
| Neat | 21319.5 |
| 1/10 | 8576 |
| 1/20 | 2304 |
| 1/40 | 1688.5 |
| 1/80 | 802 |
| 1/160 | 484.5 |

In a second set of tests, serum was used in dilutions of 1/40, 1/80, 1/160, 1/320, 1/640, 1/1280, and 1/2560 with wash buffer. Each dilution was mixed with a coated microparticle suspension as in the preceding examples. Unlike the first set of tests, the particle/sample suspensions in this second set were incubated (room temperature, ten minutes, 1,100 rpm) prior to separation. Contaminating proteins and immunoglobulins were then removed by magnetic separation. After subsequent washes and incubation with label antibody, the microparticles were analyzed on the Luminex flow cytometer, and the results are shown in Table VII.

TABLE VII

Relative Fluorescence Intensity

| Dilution | Detector Units |
|---|---|
| 1/40 | 18253.5 |
| 1/80 | 11831 |
| 1/160 | 7052.5 |
| 1/320 | 3933.5 |
| 1/640 | 2338 |
| 1/1280 | 1377.5 |
| 1/2560 | 802.5 |
| Wash Buffer | 219.5 |

The data in Tables VI and VII demonstrate that all dilutions were distinguishable from each other.

Figure 4:
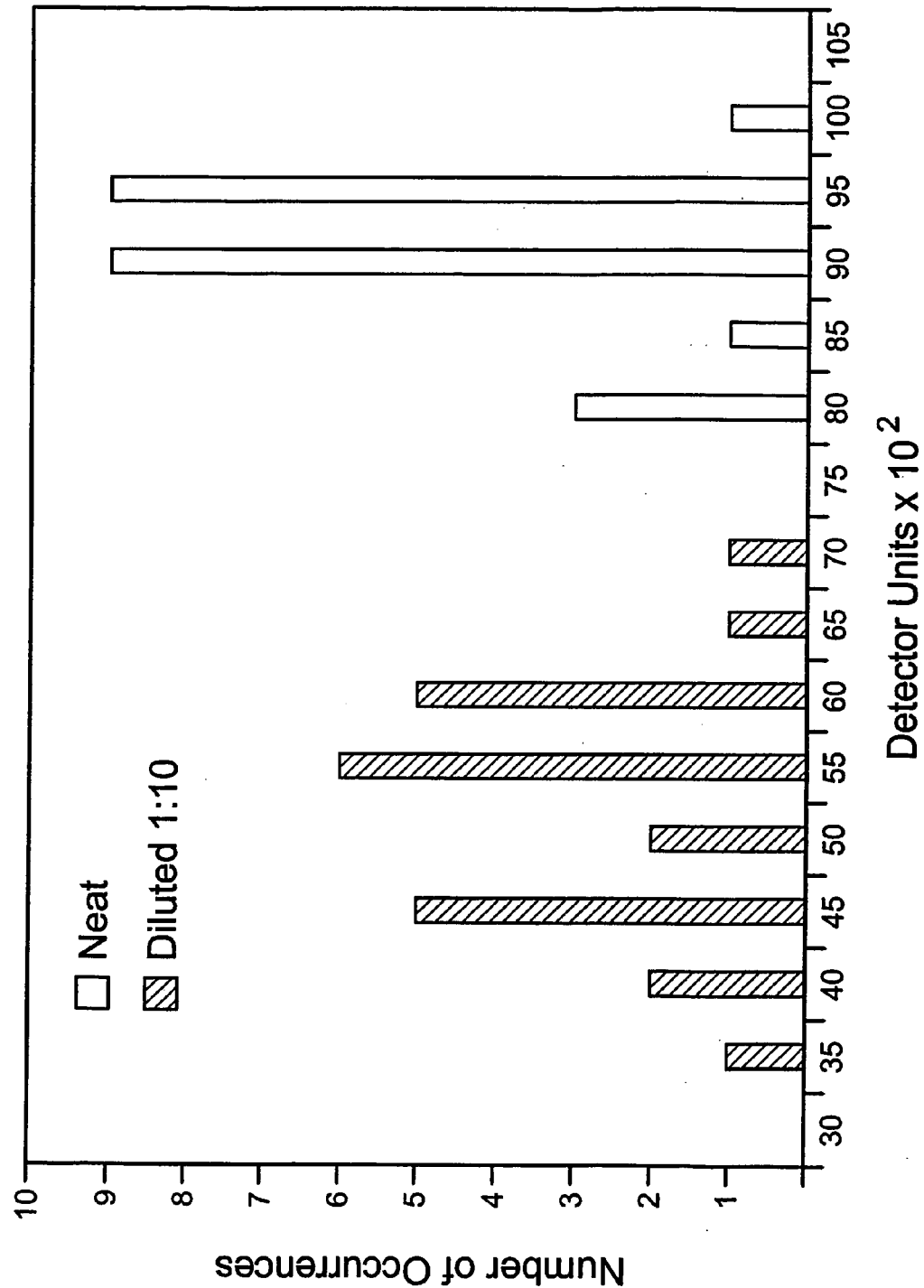
FIG. 4 is a histogram comparing FXIII levels among serum samples that are diluted with serum samples that are undiluted.

In a third set of tests, 23 serum samples, 100 μL each in volume, were used, including some that were neat (undiluted) and some that were diluted 1/10 with wash buffer. To each sample was added a coated microparticle suspension amounting to 0.26 μg of particles per sample, and the samples were separated on a magnetic plate for. 3 minutes, then aspirated and washed twice with 300 μL wash buffer. After the final wash, labeled antibody (50 μL) was added to each sample. The samples were then mixed on a shaker for ten minutes (900 rpm, 37° C.), and then separated on a magnetic plate for 3 minutes. The supernatant was aspirated and the particles were washed twice with 300 μL wash buffer. Further wash buffer (75 μL) was then added to each sample to prepare the samples for the flow cytometer. Analysis on the flow cytometer proceeded, and the results are shown in the histogram of FIG. 4, which shows the distribution of detector units among the neat and diluted samples. The horizontal axis is the number of detector units and the vertical axis is the number of samples. Filled bars are used for the diluted samples and open bars for the neat (undiluted) samples. All of the diluted samples are fully distanced from the neat samples, with no overlap between these two sets. This confirms that samples that are diluted by 1/10 can be consistently distinguished from those that are undiluted.

EXAMPLE 6

Figure 2:
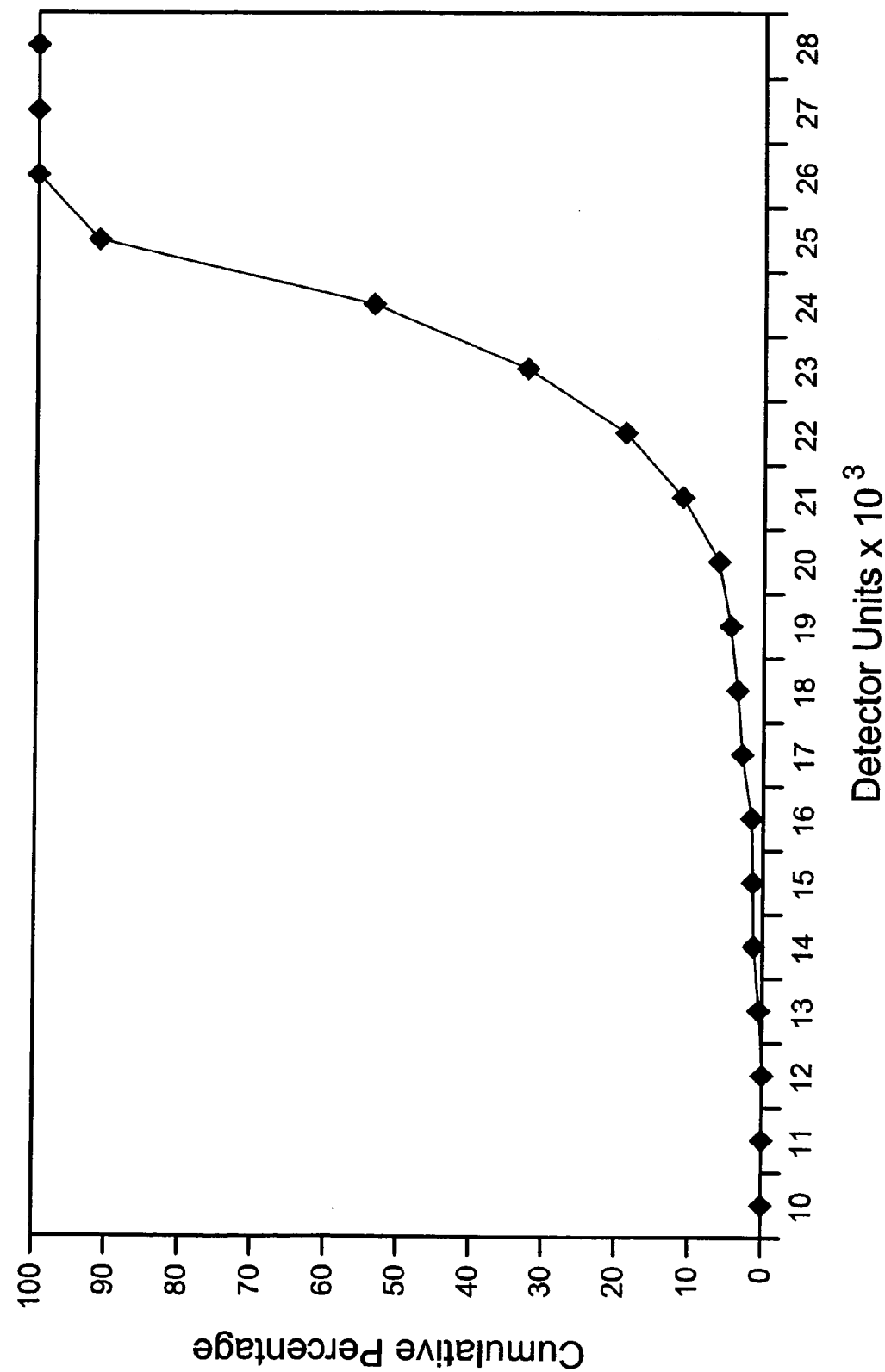
FIG. 2 is a plot showing the distribution of FXIII levels among the sera of 260 human patients.

This example illustrates the low degree of variation of FXIII among the serum samples of different human patients. Samples from 260 different individuals were tested, using the same procedures as Example 3. The distribution of results is shown in order of increasing detector units in FIG. 2, which indicates that there was little variation among the levels of FXIII throughout the samples.

The foregoing descriptions are offered primarily for purposes of illustration. Further modifications and alternatives of the materials and procedures expressed that are still within the scope of this invention above will be readily apparent to those skilled in the art.

What is claimed is:

1. A method for verifying the degree of dilution of a test sample of either serum or plasma, said method comprising analyzing said test sample for an amount of b subunit of human Factor XIII protein in said test sample, to determine a concentration of said b subunit of human Factor XIII in said test sample and comparing said concentration of b subunit of human factor XIII protein in said test sample with a concentration of b subunit of Factor XIII of a control sample of human serum or plasma having a known degree of dilution, wherein if said concentration of said test sample and said control sample are not same, then said test sample is not of the same degree of dilution as said control sample.

2. A method in accordance with claim 1 in which the amount of said b subunit in said sample is determined by immunoassay.

3. A method in accordance with claim 2 in which said immunoassay comprises contacting said sample with a capture antibody that has specific binding affinity for said b subunit, and detecting said b subunit thus captured.

4. A method in accordance with claim 2 in which said immunoassay comprises (a) contacting said sample with a solid phase to which is bound a capture antibody that has specific binding affinity for said b subunit, and (b) determining whether any binding of said b subunit to said solid phase through said capture antibody has occurred.

5. A method in accordance with claim 4 in which said solid phase is a population of particles, and step (b) comprises detecting said particles by flow cytometry.

* * * * *